United States Patent
Long et al.

(10) Patent No.: US 11,141,523 B2
(45) Date of Patent: Oct. 12, 2021

(54) WOUND DRESSINGS AND SYSTEMS FOR EFFLUENT MANAGEMENT OF TOPICAL WOUND THERAPY AND RELATED METHODS

(71) Applicant: KCI Licensing, Inc., San Antonio, TX (US)

(72) Inventors: Justin Alexander Long, Bournemouth (GB); Christopher Brian Locke, Bournemouth (GB); Timothy Mark Robinson, Blandford Forum (GB); Richard Coulthard, Verwood (GB)

(73) Assignee: KCI LICENSING, INC., San Antonio, TX (US)

( * ) Notice: Subject to any disclaimer, the term of this patent is extended or adjusted under 35 U.S.C. 154(b) by 223 days.

(21) Appl. No.: 16/171,566

(22) Filed: Oct. 26, 2018

(65) Prior Publication Data
US 2019/0125945 A1    May 2, 2019

Related U.S. Application Data

(60) Provisional application No. 62/577,505, filed on Oct. 26, 2017.

(51) Int. Cl.
*A61M 1/00* (2006.01)
*A61M 13/00* (2006.01)
(Continued)

(52) U.S. Cl.
CPC ............. *A61M 1/85* (2021.05); *A61M 1/784* (2021.05); *A61M 1/90* (2021.05); *A61M 13/003* (2013.01);
(Continued)

(58) Field of Classification Search
CPC ............ A61M 16/0087; A61M 16/009; A61M 16/12; A61M 16/122; A61M 35/30;
(Continued)

(56) References Cited

U.S. PATENT DOCUMENTS

| 10,300,180 B1 * | 5/2019 | Quisenberry ......... A61L 2/0047 |
| 2003/0050674 A1 | 3/2003 | Joshi |

(Continued)

FOREIGN PATENT DOCUMENTS

| CN | 205924317 | 2/2017 |
| EP | 2956101 | 12/2015 |

(Continued)

OTHER PUBLICATIONS

International Search Report and Written Opinion issued in Corresponding PCT Application No. PCT/US2018/051408, dated Jan. 23, 2019.

(Continued)

*Primary Examiner* — Kevin C Sirmons
*Assistant Examiner* — Antarius S Daniel
(74) *Attorney, Agent, or Firm* — Foley & Lardner LLP

(57) ABSTRACT

This disclosure includes wound dressings and systems for effluent management of topical wound therapy and related methods. Some devices, which are configured to dilute therapeutic gas effluent flowing from a dressing, comprise a therapeutic gas source configured to provide therapeutic gas to the dressing; a container comprising a sidewall that defines a chamber configured to receive therapeutic gas effluent from the dressing; a negative pressure source configured to be coupled to the container such that the negative pressure source can be activated to draw fluid from the dressing through the chamber of the container; and a diluent gas source configured to deliver a diluent gas to dilute (Continued)

therapeutic gas effluent before the therapeutic gas effluent enters the negative pressure source.

16 Claims, 2 Drawing Sheets

(51) Int. Cl.
  *B01D 53/04* (2006.01)
  *A61M 35/00* (2006.01)
(52) U.S. Cl.
  CPC .............. *A61M 35/30* (2019.05); *B01D 53/04* (2013.01); *B01D 53/0407* (2013.01); *A61M 2202/0208* (2013.01); *A61M 2202/0266* (2013.01); *A61M 2205/3337* (2013.01); *A61M 2205/7536* (2013.01); *B01D 2253/102* (2013.01); *B01D 2253/1122* (2013.01); *B01D 2256/10* (2013.01); *B01D 2257/104* (2013.01); *B01D 2259/4533* (2013.01)
(58) Field of Classification Search
  CPC ........ A61M 13/003; A61M 2202/0208; A61M 2202/0216; A61M 2202/0266; B01D 53/04; B01S 2259/4533
  See application file for complete search history.

(56) References Cited

U.S. PATENT DOCUMENTS

| | | | |
|---|---|---|---|
| 2004/0260253 A1 | 12/2004 | Rosati | |
| 2006/0200100 A1 | 9/2006 | Rosati | |
| 2009/0227969 A1 | 9/2009 | Jaeb et al. | |
| 2009/0259171 A1 | 10/2009 | Joshi et al. | |
| 2010/0069858 A1 | 3/2010 | Olson | |
| 2010/0305490 A1 | 12/2010 | Coulthard et al. | |
| 2012/0059301 A1 | 3/2012 | Franklin | |
| 2012/0209226 A1 | 8/2012 | Simmons et al. | |
| 2016/0030722 A1 | 2/2016 | Anderson et al. | |
| 2016/0166781 A1* | 6/2016 | Sarangapani | A61M 35/30 604/23 |
| 2016/0175500 A1 | 6/2016 | Cali et al. | |
| 2017/0319394 A1 | 11/2017 | Chen et al. | |
| 2019/0030226 A1* | 1/2019 | Lin | A61L 15/58 |

FOREIGN PATENT DOCUMENTS

| | | |
|---|---|---|
| TW | 200942281 | 10/2009 |
| TW | M525742 | 7/2016 |
| WO | WO 1996/032082 | 10/1996 |
| WO | WO 2009/066106 | 5/2009 |
| WO | WO 2009/097534 | 8/2009 |
| WO | WO 2009/146441 | 12/2009 |
| WO | WO 2009/158500 | 12/2009 |
| WO | WO 2011/008497 | 1/2011 |
| WO | WO 2011/008711 | 1/2011 |
| WO | WO 2013/066694 | 5/2013 |
| WO | WO 2014/144762 | 9/2014 |
| WO | WO 2015/123353 | 8/2015 |

OTHER PUBLICATIONS

International Search Report and Written Opinion issued in Corresponding PCT Application No. PCT/US2019/012250, dated May 7, 2019.

* cited by examiner

WOUND DRESSINGS AND SYSTEMS FOR EFFLUENT MANAGEMENT OF TOPICAL WOUND THERAPY AND RELATED METHODS

CROSS-REFERENCE TO RELATED APPLICATIONS

This application claims the benefit of U.S. Provisional Application No. 62/577,505, filed Oct. 26, 2017, the contents of which is incorporated into the present application in its entirety.

BACKGROUND

1. Field of Invention

The present invention relates generally to wound dressings, and more specifically, but not by way of limitation, to wound dressings and systems for effluent management of topical wound therapy and related methods.

2. Description of Related Art

Clinical studies and practice have shown that topical applications of therapeutic gas, such as, for example, oxygen, can improve wound healing, especially in chronic wounds. Topical applications of therapeutic gas can reduce tissue inflammation and/or improve tissue proliferation (e.g., improve collagen synthesis, growth factor production, angiogenesis, and/or the like).

The functional integration of technology to deliver negative pressure wound therapy (NPWT) and topical oxygen therapy presents challenges for the dissipation of oxygen effluent that exits a dressing and returns to a therapy device. For example, because oxygen effluent contains a high purity of oxygen (e.g., greater than 80 percent), the effluent can act as an accelerant to an open flame. As such, the accumulation of high-purity oxygen effluent in a therapy device may be undesirable and/or potentially hazardous.

Thus, while the clinical benefits of topical applications of therapeutic gas, and in particular, therapeutic oxygen, are known, proper and safe management of therapeutic oxygen effluent may benefit healthcare providers, caregivers, and patients.

SUMMARY

Some embodiments of the present devices, which are configured to dilute therapeutic gas effluent flowing from a dressing, comprise a therapeutic gas source configured to provide therapeutic gas to the dressing; a first outlet configured to be in fluid communication with the therapeutic gas source; a container comprising a sidewall that defines a chamber configured to receive therapeutic gas effluent from the dressing; a first inlet configured to be in fluid communication with the chamber and to receive therapeutic gas effluent from the dressing; a negative pressure source configured to be coupled to the container such that the negative pressure source can be activated to draw fluid from the dressing through the chamber of the container, wherein the negative pressure source comprises: an inlet through which gas is received into the negative pressure source; and an outlet through which gas exits the negative pressure source; and a diluent gas source coupled to the device and configured to deliver a diluent gas to dilute therapeutic gas effluent before the therapeutic gas effluent enters through the inlet of the negative pressure source.

In some embodiments of the present devices, the diluent gas source is configured to deliver the diluent gas between the dressing and the chamber. In some embodiments of the present devices, the diluent gas source is configured to deliver the diluent gas between the negative pressure source and the chamber. In some embodiments of the present devices, the diluent gas source is configured to deliver the diluent gas to the chamber.

In some embodiments of the present devices, the therapeutic gas source comprises an oxygen source and the therapeutic gas comprises oxygen. In some embodiments of the present devices, the oxygen source comprises an oxygen concentrator configured to receive atmospheric air and remove nitrogen from the air. In some embodiments of the present devices, the diluent gas source is integral with the therapeutic gas source, and the diluent gas comprises the removed nitrogen.

In some embodiments of the present devices, the chamber comprises an oxygen-sorbent material. In some embodiments of the present devices, the oxygen-sorbent material comprises one or more elements selected from the group of elements consisting of: iron, sodium chloride, and activated carbon. In some embodiments of the present devices, the container comprises one or more oxygen filters configured to absorb oxygen. In some embodiments of the present devices, at least one of the one or more oxygen filters is impregnated with one or more elements selected from the group of elements consisting of: pyrogallol, iron, silver chloride, and ascorbic acid. In some embodiments of the present devices, the container comprises a first one-way valve configured to: permit communication of gas out of the chamber through the first valve; and prevent communication of gas into the chamber through the first valve. In some embodiments of the present devices, the chamber comprises one or more baffles, impellers, and/or a screw mixer configured to encourage mixing of the diluent gas and therapeutic gas effluent within the chamber.

In some embodiments of the present devices, the oxygen source is configured to provide oxygen to the dressing at a volumetric flow rate of at least 0.25 liters per minute and at a purity of at least 70 percent. In some embodiments of the present devices, the oxygen source is configured to provide oxygen to the dressing at a volumetric flow rate of approximately 3 to 50 milliliters per hour and at a purity of at least 70 percent.

In some embodiments of the present devices, the diluent gas source comprises a reservoir containing the diluent gas, wherein the reservoir is configured to be coupled to the container in fluid communication with the chamber to provide the diluent gas to the chamber. In some embodiments of the present devices, the diluent gas comprises nitrogen. In some embodiments of the present devices, the diluent gas comprises atmospheric air and the diluent gas source comprises a second one-way valve in fluid communication with the chamber and configured to: permit communication of the diluent gas into the chamber through the second valve; and prevent communication of the diluent gas out of the chamber through the second valve.

Some embodiments of the present devices comprise one or more first conduits configured to be coupled to the first outlet to permit fluid communication of therapeutic gas between the therapeutic gas source and the dressing. Some embodiments of the present devices comprise one or more second conduits configured to be coupled to the first inlet to permit fluid communication of therapeutic gas effluent between the dressing and the chamber. In some embodiments of the present devices, at least one of the one or more first conduits and/or at least one of the one or more second conduits comprise one or more valves configured to block fluid communication in the respective conduit through the valve in response to detecting a fire within the respective conduit.

Some embodiments of the present devices comprise one or more third conduits configured to be coupled between the diluent gas source and at least one of the one or more second conduits to permit fluid communication of the diluent gas between the diluent gas source and the chamber. Some embodiments of the present devices comprise one or more fourth conduits configured to be coupled between the diluent gas source and the container to permit fluid communication of the diluent gas between the diluent gas source and the chamber.

Some embodiments of the present devices comprise a second outlet configured to be in fluid communication with the diluent gas source; one or more fifth conduits configured to be coupled to the second outlet to permit fluid communication of the diluent gas between the diluent gas source and the dressing.

Some embodiments of the present devices comprise one or more sixth conduits configured to be coupled between the diluent gas source and the negative pressure source to permit fluid communication of the diluent gas between the diluent gas source and the negative pressure source.

Some embodiments of the present devices comprise a wound irrigation device configured to provide wound irrigation fluid to the dressing. In some embodiments of the present devices, the wound irrigation fluid comprises one or more elements selected from the group consisting of saline, an antimicrobial, and bleach. Some embodiments of the present devices comprise a third outlet configured to be in fluid communication with the wound irrigation device; one or more seventh conduits configured to be coupled to the third outlet to permit fluid communication of wound irrigation fluid between the wound irrigation device and the dressing. In some embodiments of the present devices, the wound irrigation device is configured to be in fluid communication with the first outlet. Some embodiments of the present devices comprise a valve movable between a first position, in which the valve permits therapeutic gas from the therapeutic gas source through the first outlet, and a second position, in which the valve permits wound irrigation fluid from the wound irrigation device through the first outlet.

Some embodiments of the present systems comprise a dressing comprising: a gas-occlusive layer configured to be coupled to tissue surrounding target tissue such that an interior volume is defined between the gas-occlusive layer and the target tissue; and a body defining one or more ports configured to provide fluid communication to the interior volume through the gas-occlusive layer; a therapeutic gas source configured to be coupled to the dressing in fluid communication with the interior volume to provide therapeutic gas to the interior volume; a negative pressure source configured to be coupled to the dressing such that the negative pressure source can be activated to draw gas from the interior volume; and a diluent gas source configured to be coupled to the system between the interior volume and the negative pressure source to deliver a diluent gas to dilute therapeutic gas effluent as or after the therapeutic gas effluent flows out of the interior volume.

Some embodiments of the present systems comprise, for at least one of the one or more ports, a filter configured to filter fluid that flows through the port. In some embodiments of the present systems, the filter comprises a layer of material that is bonded to an upper surface or a lower surface of the gas-occlusive layer. In some embodiments of the present systems, the filter is configured to permit communication of therapeutic gas effluent out of the interior volume through the port and restrict communication of exudate out of the interior volume through the port.

Some embodiments of the present systems comprise a dressing comprising: a gas-occlusive layer configured to be coupled to tissue surrounding target tissue such that an interior volume is defined between the gas-occlusive layer and the target tissue; and a body defining one or more ports configured to provide fluid communication to the interior volume through the gas-occlusive layer; a therapeutic gas source configured to be coupled to the dressing in fluid communication with the interior volume to provide therapeutic gas to the interior volume; a container outside the interior volume, the container comprising a sidewall that defines a chamber configured to be coupled to the dressing in fluid communication with the interior volume to receive therapeutic gas effluent from the interior volume; a negative pressure source configured to be coupled to the container such that the negative pressure source can be activated to draw fluid from the interior volume through the chamber of the container; and a diluent gas source configured to be coupled to the system between the interior volume and the negative pressure source to deliver a diluent gas to dilute therapeutic gas effluent as or after the therapeutic gas effluent flows out of the interior volume. In some embodiments of the present systems, the container comprises an outlet in fluid communication with the negative pressure source, the outlet having a filter configured to filter fluid that flows through the outlet. In some embodiments of the present systems, the filter comprises a layer of material that is bonded to the sidewall of the container. In some embodiments of the present systems, the filter is configured to permit communication of therapeutic gas effluent out of the chamber through the outlet and restrict communication of exudate out of the chamber through the outlet. In some embodiments of the present systems, the diluent gas source is configured to be coupled to the system between the dressing and the container.

In some embodiments of the present systems, the diluent gas source is configured to be coupled to the system between the container and the negative pressure source. In some embodiments of the present systems, the diluent gas source is configured to be coupled to the container.

In some embodiments of the present systems, the therapeutic gas source comprises an oxygen source and the therapeutic gas comprises oxygen. In some embodiments of the present systems, the oxygen source comprises an oxygen concentrator configured to receive atmospheric air and remove nitrogen from the air. In some embodiments of the present systems, the diluent gas source is integral with the therapeutic gas source, and the diluent gas comprises the removed nitrogen.

In some embodiments of the present systems, the chamber comprises an oxygen-sorbent material. In some embodiments of the present systems, the oxygen-sorbent material comprises one or more elements selected from the group of elements consisting of: iron, sodium chloride, and activated carbon. In some embodiments of the present systems, the container comprises one or more oxygen filters configured to absorb oxygen. In some embodiments of the present systems, at least one of the one or more oxygen filters is impregnated with one or more elements selected from the group of elements consisting of: pyrogallol, iron, silver chloride, and ascorbic acid.

In some embodiments of the present systems, the oxygen source is configured to provide oxygen to the interior volume at a volumetric flow rate of at least 0.25 liters per minute and at a purity of at least 75 percent. In some embodiments of the present systems, the oxygen source is configured to provide oxygen to the interior volume at a volumetric flow rate of approximately 3 to 50 milliliters per hour and at a purity of at least 75 percent.

In some embodiments of the present systems, the diluent gas source comprises a reservoir containing the diluent gas, wherein the reservoir is configured to be coupled to the container in fluid communication with the chamber to provide the diluent gas to the chamber. In some embodiments of the present systems, the diluent gas comprises nitrogen. In some embodiments of the present systems, the container comprises a first one-way valve configured to: permit communication of gas out of the chamber through the first valve; and prevent communication of gas into the chamber through the first valve. In some embodiments of the present systems, the diluent gas comprises atmospheric air and the diluent gas source comprises a second one-way valve in fluid communication with the chamber and configured to: permit communication of the diluent gas into the chamber through the second valve; and prevent communication of the diluent gas out of the chamber through the second valve.

In some embodiments of the present systems, the chamber comprises one or more baffles, impellers, and/or a screw mixer configured to encourage mixing of the diluent gas and therapeutic gas effluent within the chamber.

Some embodiments of the present systems comprise one or more first conduits configured to be coupled between the therapeutic gas source and the dressing to permit fluid communication of therapeutic gas between the therapeutic gas source and the interior volume. Some embodiments of the present systems comprise one or more second conduits configured to be coupled between the dressing and the container to permit fluid communication of therapeutic gas effluent between the interior volume and the chamber.

In some embodiments of the present systems, at least one of the one or more first conduits and/or at least one of the one or more second conduits comprise one or more valves configured to block fluid communication in the respective conduit through the valve in response to detecting a fire within the respective conduit. Some embodiments of the present systems comprise one or more third conduits configured to be coupled between the diluent gas source and at least one of the one or more second conduits to permit fluid communication of the diluent gas between the diluent gas source and the chamber. Some embodiments of the present systems comprise one or more fourth conduits configured to be coupled between the diluent gas source and the container to permit fluid communication of the diluent gas between the diluent gas source and the chamber. Some embodiments of the present systems comprise one or more fifth conduits configured to be coupled between the diluent gas source and the dressing to permit fluid communication of the diluent gas between the diluent gas source and the body defining the one or more ports of the dressing. Some embodiments of the present systems comprise one or more sixth conduits configured to be coupled between the diluent gas source and the negative pressure source to permit fluid communication of the diluent gas between the diluent gas source and the negative pressure source.

In some embodiments of the present systems, the body defining the one or more ports comprises a valve assembly having: a first inlet configured to be in fluid communication with the interior volume and to receive therapeutic gas effluent from the interior volume; a second inlet configured to be in fluid communication with the diluent gas source to receive the diluent gas from the diluent gas source; and an outlet configured be coupled to the container in fluid communication with the chamber to permit fluid communication of the diluent gas and therapeutic gas effluent into the chamber. In some embodiments of the present systems, the one or more second conduits is configured to be coupled between the container and the outlet to permit fluid communication of therapeutic gas effluent between the outlet and the chamber of the container; and the one or more fifth conduits is configured to be coupled between the therapeutic gas source and the second inlet to permit fluid communication of the diluent gas between the therapeutic gas source and the second inlet. In some embodiments of the present systems, the first inlet comprises a one-way valve configured to: permit communication of gas out of the interior volume through the valve; and prevent communication of gas into the interior volume through the valve.

Some embodiments of the present systems comprise a wound irrigation device configured to be in fluid communication with the interior volume to provide wound irrigation fluid to the interior volume. In some embodiments of the present systems, the wound irrigation fluid comprises one or more elements selected from the group consisting of saline, an antimicrobial, and bleach. Some embodiments of the present systems comprise one or more seventh conduits configured to be coupled between the wound irrigation device and the dressing to permit fluid communication of wound irrigation fluid between the wound irrigation device and the interior volume.

Some embodiments of the present methods, for diluting therapeutic gas effluent flowing from a dressing, comprise coupling a dressing to a patient's tissue, the dressing comprising a gas-occlusive layer configured to be coupled to tissue surrounding target tissue such that an interior volume is defined between the gas-occlusive layer and the target tissue; providing therapeutic gas to the interior volume; removing therapeutic gas effluent from the interior volume; and mixing the removed therapeutic gas effluent with a diluent gas.

In some embodiments of the present methods, the removed therapeutic gas effluent is mixed with the diluent gas in a container outside the interior volume. In some embodiments of the present methods, the therapeutic gas effluent is removed from the interior volume by applying a negative pressure within the interior volume. In some embodiments of the present methods, providing therapeutic gas to the interior volume and removing therapeutic gas effluent from the interior volume occurs simultaneously. In some embodiments of the present methods, providing therapeutic gas and removing therapeutic gas effluent occurs simultaneously for a duration of 3 to 4 hours.

Some embodiments of the present methods comprise providing wound irrigation fluid to the interior volume. In some embodiments of the present methods, the wound irrigation fluid is provided for a duration of 5 to 15 minutes. Some embodiments of the present methods comprise removing wound irrigation fluid from the interior volume.

The term "coupled" is defined as connected, although not necessarily directly, and not necessarily mechanically; two items that are "coupled" may be unitary with each other. The terms "a" and "an" are defined as one or more unless this disclosure explicitly requires otherwise. The term "substantially" is defined as largely but not necessarily wholly what is specified (and includes what is specified; e.g., substantially 90 degrees includes 90 degrees and substantially parallel includes parallel), as understood by a person of ordinary skill in the art. In any disclosed embodiment, the term "substantially" may be substituted with "within [a percentage] of" what is specified, where the percentage includes 0.1, 1, 5, and 10 percent.

The phrase "and/or" means and or. The phrase "and/or" includes any and all combinations of one or more of the associated listed items. To illustrate, A, B, and/or C includes: A alone, B alone, C alone, a combination of A and B, a combination of A and C, a combination of B and C, or a combination of A, B, and C. In other words, "and/or" operates as an inclusive or.

The terms "comprise" (and any form of comprise, such as "comprises" and "comprising"), "have" (and any form of have, such as "has" and "having"), and "include" (and any form of include, such as "includes" and "including") are open-ended linking verbs. As a result, an apparatus that "comprises," "has," or "includes" one or more elements possesses those one or more elements, but is not limited to possessing only those elements. Likewise, a method that "comprises," "has," or "includes," one or more steps possesses those one or more steps, but is not limited to possessing only those one or more steps.

Any embodiment of any of the apparatuses, systems, and methods can consist of or consist essentially of—rather than comprise/have/include—any of the described steps, elements, and/or features. Thus, in any of the claims, the term "consisting of" or "consisting essentially of" can be substituted for any of the open-ended linking verbs recited above, in order to change the scope of a given claim from what it would otherwise be using the open-ended linking verb.

The feature or features of one embodiment may be applied to other embodiments, even though not described or illustrated, unless expressly prohibited by this disclosure or the nature of the embodiments.

Further, an apparatus that is configured in a certain way is configured in at least that way, but it can also be configured in other ways than those specifically described.

Some details associated with the embodiments are described above, and others are described below.

BRIEF DESCRIPTION OF THE DRAWINGS

The following drawings illustrate by way of example and not limitation. For the sake of brevity and clarity, every feature of a given structure is not always labeled in every figure in which that structure appears. Identical reference numbers do not necessarily indicate an identical structure. Rather, the same reference number may be used to indicate a similar feature or a feature with similar functionality, as may non-identical reference numbers. The figures are drawn to scale (unless otherwise noted), meaning the sizes of the depicted elements are accurate relative to each other for at least the embodiment depicted in the figures. Figures having schematic views are not drawn to scale.

DETAILED DESCRIPTION

Figure 1:
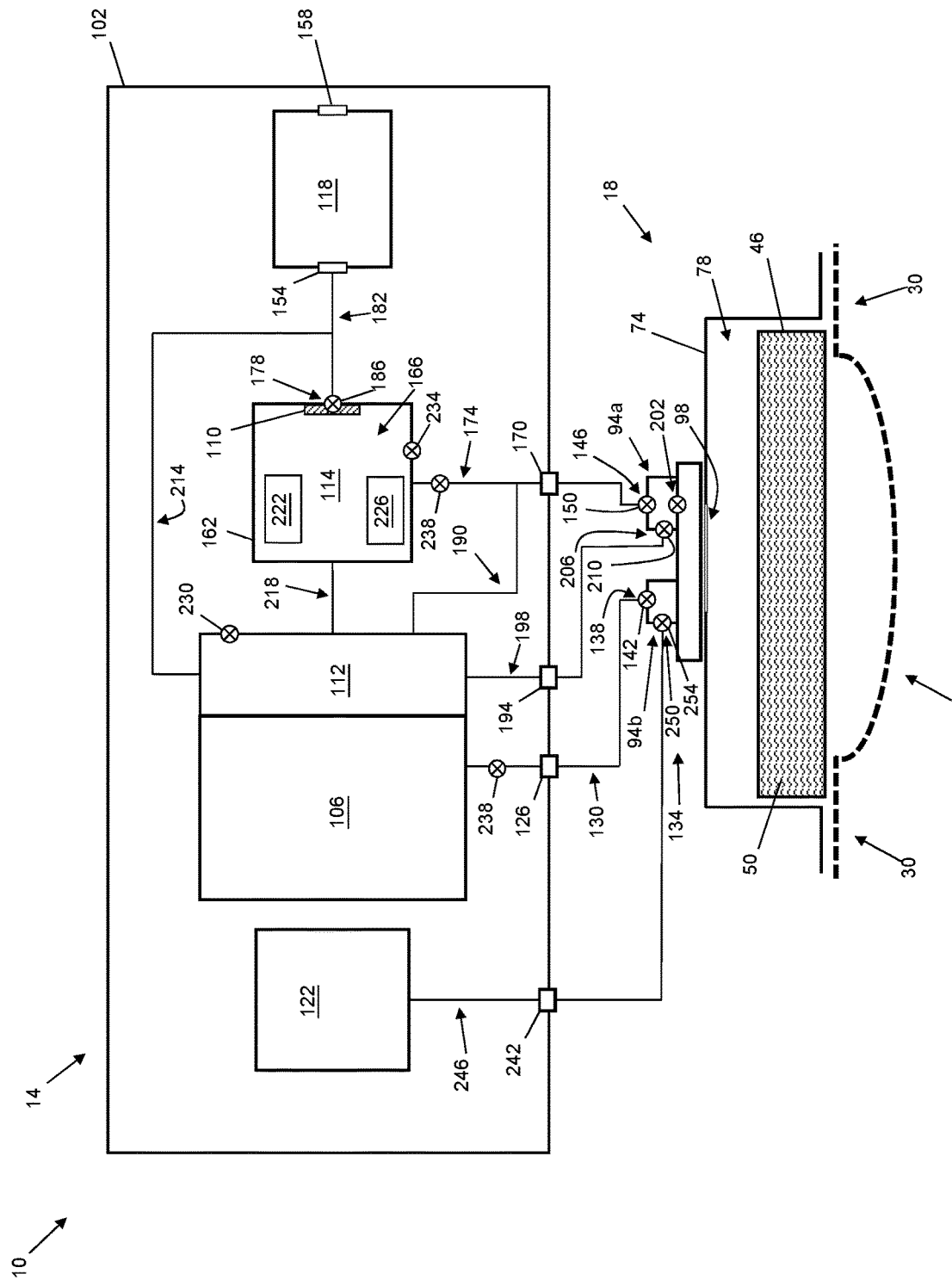
FIG. 1 is a schematic view of a first embodiment of the present systems.

Referring to FIG. 1, shown therein and designated by the reference numeral 10 is one embodiment of the present systems for providing topical wound therapy. System 10 includes a wound therapy device 14 and a wound dressing 18 configured to be coupled to target tissue 22 and/or to tissue 30 surrounding the target tissue to facilitate delivery of therapeutic gas to the target tissue.

The term "target tissue" as used herein can broadly refer to a wound (e.g., open or closed), a tissue disorder, and/or the like located on or within tissue, such as, for example, bone tissue, adipose tissue, muscle tissue, neural tissue, dermal tissue, vascular tissue, connective tissue, cartilage, tendons, ligaments, and/or the like. The term "target tissue" as used herein can also refer to areas of tissue that are not necessarily wounded or exhibit a disorder, but include tissue that would benefit from tissue generation. The term "wound" as used herein can refer to a chronic, subacute, acute, traumatic, and/or dehisced incision, laceration, puncture, avulsion, and/or the like, a partial-thickness and/or full thickness burn, an ulcer (e.g., diabetic, pressure, venous, and/or the like), flap, and/or graft.

Dressing 18 can include one or more manifolds 46 configured to allow communication of therapeutic gas to target tissue 22 and/or allow communication of exudate away from the target tissue. Manifold 46 can be configured to be in contact with target tissue 22. For example, manifold 46 may be disposed over target tissue 22 such that the manifold fills at least a portion of a recess defined by the target tissue.

Manifold 46 may be porous. For example, each manifold 46 can define a plurality of gas passageways 50 to distribute therapeutic gas across the manifold, to collect exudate from target tissue 22 across the manifold, and/or to promote granulation of the target tissue. Each gas passageway 50 can comprise a width ranging approximately 400 to approximately 600 microns. Plurality of gas passageways 50 of each manifold 46 can be interconnected to improve distribution and/or collection of fluids across the manifold. For example, gas passageways 50 can be defined by an open-cell foam (e.g., reticulated foam), tissue paper, gauze, a non-woven textile (e.g., felt), and/or the like.

Manifold 46 can comprise any suitable material, such as, for example, polyethylene, a polyolefin, a polyether, polyurethane, a co-polyester, a copolymer thereof, or a blend thereof. For example, in embodiments where manifold 46 comprises a foam, such a foam may be polyether-based polyurethane foam. Manifold 46 can comprise any suitable planform shape, planform area, thickness, and/or the like that is appropriate to treat target tissue 22.

A non-limiting example of manifold 46 includes GRANUFOAM™ Dressings, which are commercially available from Kinetic Concepts Inc., of San Antonio, Tex., USA.

Dressing 18 can include a gas-occlusive layer 74. Gas-occlusive layer 74 can be configured to be disposed over one or more manifolds 46 and coupled to tissue 30 surrounding target tissue 22 such that an interior volume 78 is defined between the gas-occlusive layer and the target tissue. Gas-occlusive layer 74 can be coupled to tissue 30 surrounding target tissue 22 such that the gas-occlusive layer 74 limits the escape of therapeutic gas and/or exudate from interior volume 78 between the gas-occlusive layer and the tissue surrounding the target tissue. For example, a tissue-facing surface of gas-occlusive layer 74 can comprise an adhesive, such as, for example, an acrylic adhesive, polyurethane gel adhesive, silicone adhesive, a combination thereof, and/or the like, configured to couple the gas-occlusive layer to tissue 30 surrounding target tissue 22.

Gas-occlusive layer 74 may comprise a flexible film, such as, for example, a hydrocolloid sheet. Gas-occlusive layer 74 can comprise any suitable material that limits escape of therapeutic gas and/or exudate through the gas-occlusive layer, such as, for example, polyurethane, polyethylene, polyvinyl acetate, polyvinyl chloride, polyvinylidene chloride, isobutylene, a halogenated isomer (e.g., chlorobutyl and/or bromobutyl), epichlorohydrin, a copolymer thereof, or a blend thereof. Gas-occlusive layer 74 can comprise any suitable planform shape, planform area, thickness, and/or the like that is appropriate to treat target tissue 22. For example, gas-occlusive layer 74 can comprise a thickness that is approximately any one of, or between approximately any two of the following: 5, 10, 15, 20, 25, 30, 35, 40, 45, 50, 55, and 60 micrometers.

Gas-occlusive layer 74 can comprise one or more openings 98 configured to permit communication of therapeutic gas into and/or therapeutic gas effluent out of interior volume 78 of dressing 18. One or more openings 98 may be configured to permit communication of exudate out of interior volume 78 of dressing 18.

Device 14 can comprise a housing 102 configured to hold a therapeutic gas source 106, a diluent gas source 112, a container 114, a negative pressure source 118, and, optionally, a wound irrigation device 122.

Therapeutic gas source 106 can be configured to provide therapeutic gas to dressing 18. More particularly, therapeutic gas source can be configured to be coupled to dressing 18 in fluid communication with interior volume 78 to provide therapeutic gas to the interior volume. For example, device 14 comprises a first outlet 126 configured to be in fluid communication with therapeutic gas source 106. System 10 can comprise one or more therapeutic gas ("TG") conduits 130 configured to be coupled between therapeutic gas source 106 and dressing 18 to permit fluid communication of therapeutic gas between the therapeutic gas source and interior volume 78. For example, TG conduit(s) 130 can be configured to be coupled to first outlet 126 of device 14 to permit fluid communication of therapeutic gas between therapeutic gas source 106 and dressing 18.

Dressing 18 may comprise a body 134 defining one or more outlet ports 94*a* and one or more inlet ports 94*b* configured to provide fluid communication to interior volume 78 through gas-occlusive layer 74. For example, therapeutic gas can be delivered to interior volume 78 via inlet port(s) 94*b* of body 134. More particularly, inlet port(s) 94*b* of body 134 may have a first inlet 138 configured to be in fluid communication with interior volume 78 and to receive therapeutic gas from therapeutic gas source 106. For example, first inlet 138 can comprise a one-way valve 142 configured to permit communication of therapeutic gas into interior volume 78 through the valve and prevent communication of therapeutic gas out of the interior volume through the valve.

Therapeutic gas may be introduced into interior volume 78 to treat target tissue 22. After sufficient exposure to target tissue 22, therapeutic gas within interior volume 78 may be removed from the interior volume—the removed therapeutic gas is called "therapeutic gas effluent." For example, therapeutic gas effluent can be removed from interior volume 78 via outlet port(s) 94*a* of body 134. More particularly, outlet port(s) 94*a* of body 134 may have an outlet 146 configured to be in fluid communication with interior volume 78 and to permit flow of therapeutic gas effluent and/or exudate out of the interior volume. For example, outlet 146 can comprise a one-way valve 150 configured to permit communication of therapeutic gas effluent and/or exudate out of interior volume 78 through the valve and prevent communication of fluid into the interior volume through the valve.

Body 134 can be configured to be releasably coupled to wound therapy device 14 and/or dressing 18 such that the device can be decoupled from the dressing without removing the dressing from target tissue 22 and/or tissue 30 surrounding the target tissue. For example, an adhesive applied to body 134 may seal the body around opening 98 of gas-occlusive layer 74 in order to minimize the diffusion of fluid between the body and the gas-occlusive layer.

A non-limiting example of body 134 includes the T.R.A.C.™ Pad, which is commercially available from Kinetic Concepts Inc., of San Antonio, Tex., USA.

Therapeutic gas source 106 can be configured to supply therapeutic gas to dressing 18 at a volumetric flow rate of at least approximately 0.25 liters per minute (L/min), such as, for example, at least approximately any one of, or between approximately any two the following: 0.25, 1, 2, 3, 4, 5, 10, 20, 30, 40, and 50 L/min. Therapeutic gas source 106 can be configured to supply any gas, such as, for example, oxygen, that is suitable for treating target tissue 22. Therapeutic gas supplied by therapeutic gas source 106 can comprise a high oxygen concentration, such as an oxygen concentration of at least 70 percent (e.g., 70, 75, 80, 85, 90, 92, 94, 96, 98, 99, 99.9, 99.99 or more percent). At least due to the high concentration of oxygen within therapeutic gas, which can act as an accelerant to an open flame, system 10 is configured to dilute therapeutic gas effluent to reduce the purity of oxygen as or after the effluent is removed from interior volume 78, as described in further detail below. In this way and others, system 10 improves the safety of topical high-purity oxygen wound therapy.

Therapeutic gas source 106 can comprise any suitable device configured to supply therapeutic gas to dressing 18 at one or more of the volumetric flow rates and/or oxygen concentrations described herein, such as, for example, an electrolytic oxygen source (e.g., an oxygen concentrator), a liquid oxygen reservoir, a reservoir having compressed oxygen gas, and/or the like. In embodiments where therapeutic gas source 106 comprises an oxygen concentrator, the therapeutic gas source may be configured to receive atmospheric air and remove nitrogen from the air (e.g., via one or more filters and/or sieve beds).

Device 14 includes a negative pressure source 118 configured to be in fluid communication with dressing 18 such that the negative pressure source can be activated to draw fluid from interior volume 78. For example, negative pressure source 118 includes an inlet 154 through which gas is received into the negative pressure source and an outlet 158 through which gas exits the negative pressure source. Negative pressure source 118 can be configured to provide negative pressure within interior volume 78 of dressing 18 such that the volume of the interior volume is reduced and/or negative pressure is applied to target tissue 22 and/or tissue 30 surrounding the target tissue to improve wound healing and/or sealing between the dressing and tissue surrounding the target tissue. As used herein, "negative pressure" can refer to a pressure that is less than a local ambient pressure, such as less than atmospheric pressure. Negative pressure source 118 can comprise a reservoir of gas held at a negative pressure. Negative pressure source 118 may comprise a mechanically and/or electrically-powered device, such as, for example, a vacuum pump, a suction pump, a wall suction port, a micro-pump, and/or the like that can reduce pressure within dressing 18 and/or a container (e.g., 114).

In some embodiments, device 14 can comprise a container 114. For example, container 114 comprises a sidewall 162 that defines a chamber 166 configured to receive therapeutic gas effluent and/or exudate from dressing 18. As shown in FIG. 1, container 114 is disposed outside of interior volume 78.

Chamber 166 can be configured to be coupled to dressing 18 in fluid communication with interior volume 78 to receive therapeutic gas effluent and/or exudate from the interior volume. For example, device 14 can include a first inlet 170 configured to be in fluid communication with chamber 166 and to receive therapeutic gas effluent and/or exudate from dressing 18. System 10 may comprise one or more effluent conduits 174 configured to be coupled between dressing 18 and container 114 (e.g., between interior volume 78 and chamber 166) to permit fluid communication between the interior volume and the chamber. For example, effluent conduit(s) 174 may be configured to be coupled between and/or to container 114 and/or outlet port(s) 94a of body 134 to permit fluid communication between the outlet port(s) and chamber 166 of the container. Further, effluent conduit(s) 174 can be configured to be coupled to first inlet 170 of device 14 to permit fluid communication between dressing 18 and chamber 166.

Negative pressure source 118 can be configured to be coupled to container 114 such that, when the negative pressure source is activated, the negative pressure source draws fluid from dressing 18, and more particularly, from interior volume 78, through chamber 166 of the container to inlet 154 of the negative pressure source.

Container 114 can comprise an outlet 178 configured to be in fluid communication with inlet 154 of negative pressure source 118 via one or more conduits 182. Outlet 178 of container 114 can comprise a one-way check valve 186 configured to permit communication of gas out of chamber 166 through the valve and prevent communication of gas into the chamber through the valve. Outlet 178 can comprise a filter 110 configured to filter fluid that flows through the outlet. For example, filter 110 can be sterile such that the filter provides a viral and/or bacterial barrier. Filter 110 can comprise a layer of material that is bonded to sidewall 162 of container 114. Filter 110 can comprise any suitable material, such as, for example, polytetrafluoroethylene (PTFE) (e.g., an expanded PTFE), a polyester, a polyamide, polyolefin, a copolymer thereof, a blend thereof, and/or the like. Filter 110 can have a backing material, such as, for example, a non-woven textile, comprising a polyester, a polyamide, and/or the like. Filter 110 may comprise a hydrophobic material. To illustrate, filter 110 can be configured to allow communication of therapeutic gas effluent out of chamber 166 through outlet 178 and restrict communication of liquid exudate out of the chamber through the outlet. In at least this way, filter 110 prevents liquid exudate from flowing to negative pressure source 118. Instead, liquid exudate remains within chamber 166 of container 114.

Filter 110 can comprise a pore size of approximately 0.05 to 0.15 micrometers (e.g., approximately any one of or between any two of the following: 0.05, 0.07, 0.09, 0.10, 0.11, 0.13, and 0.15 micrometers). A non-limiting example of filter 110 includes GORE® Microfiltration Media for Medical Devices, which is commercially available from W. L. Gore & Associates, Inc., of Newark, Del., USA.

Device 14 comprises a diluent gas source 112 configured to be coupled to system 10 (e.g., coupled to one or more components of device 14) between interior volume 78 and negative pressure source 118 to deliver a diluent gas to dilute therapeutic gas effluent as or after the therapeutic gas effluent flows out of the interior volume, but before the therapeutic gas effluent enters inlet 154 of the negative pressure source. As shown in FIG. 1, diluent gas source 112 can be configured to deliver diluent gas to one or more conduits (e.g., 174 and/or 182), to body 134, and/or directly to container 114 to dilute therapeutic gas effluent flowing from interior volume 78.

Diluent gas source 112 can comprise any suitable device configured to deliver a substance, such as, for example, nitrogen gas, that reduces the purity of oxygen within therapeutic gas effluent. For example, diluent gas source can comprise a reservoir containing diluent gas. Such a reservoir can be configured to be coupled to container 114 in fluid communication with chamber 166 to provide diluent gas to the chamber. In embodiments where therapeutic gas source 106 comprises an oxygen concentrator configured to remove nitrogen from atmospheric air, diluent gas source 112 may be integral with the therapeutic gas source such that the diluent gas provided by the diluent gas source comprises the nitrogen removed by the therapeutic gas source.

As shown in FIG. 1, diluent gas source 112 can be configured to deliver diluent gas between dressing 18 (e.g., interior volume 78) and container 114 (e.g., chamber 166). For example, system 10 can comprise one or more first diluent conduits 190 configured to be coupled between diluent gas source 112 and at least one of effluent conduit(s) 174 to permit fluid communication of diluent gas between the diluent gas source and chamber 166. As shown in FIG. 1, first diluent conduit(s) 190 can be contained within housing 102 of device 14. Therapeutic gas effluent within effluent conduit(s) 174 can mix with diluent gas supplied by diluent gas source 112 (e.g., via first diluent conduit(s) 190) to reduce the purity of oxygen within therapeutic gas effluent. In this way and others, the concentration of oxygen within therapeutic gas effluent can be reduced to approximately 20 percent before the mixture of therapeutic gas effluent and diluent gas enters inlet 154 of negative pressure source 118.

Device 14 can include a second outlet 194 configured to be in fluid communication with diluent gas source 112. For example, system 10 can include one or more second diluent conduits 198 configured to be coupled between diluent gas source 112 and dressing 18 (e.g., coupled to second outlet 194 and/or to outlet port(s) 94a of body 134) to permit fluid communication of diluent gas between diluent gas source 112 and dressing 14 (e.g., the body). For example, outlet port(s) 94a comprises an inlet 202 configured to be in fluid communication with interior volume 78 and to receive therapeutic gas effluent from the interior volume. For example, first inlet 202 can comprise a one-way valve configured to permit communication of fluid (e.g., therapeutic gas effluent and/or exudate) out of interior volume 78 through the valve and prevent communication of fluid into the interior volume through the valve. Outlet port(s) 94a can comprise a second inlet 206 having a one-way valve 210 configured to be in fluid communication with diluent gas source 112 to receive diluent gas from the diluent gas source. Outlet port(s) 94a can be configured to allow fluid through first inlet 202 and second inlet 206 simultaneously such that, as therapeutic gas effluent and/or exudate exit interior volume 78 (e.g., via the first inlet of the outlet port(s)), the therapeutic gas effluent mixes with diluent gas supplied by diluent gas source 112 (e.g., via the second inlet of the outlet port(s)) to reduce the purity of oxygen within therapeutic gas effluent. Thereafter, the resulting mixture of diluent gas, therapeutic gas effluent, and exudate can flow through outlet 146 of outlet port(s) 94a toward chamber 166 of container 114, where the therapeutic gas effluent and the diluent gas can be separated from the exudate (e.g., via filter 110). In this way and others, the concentration of oxygen within therapeutic gas effluent is reduced to approximately 20 percent before the mixture of therapeutic gas effluent and diluent gas enters inlet 154 of negative pressure source 118.

As shown in FIG. 1, diluent gas source 112 can be configured to deliver diluent gas between negative pressure source 118 and chamber 166 of container 114. For example, system 10 may include one or more third diluent conduits 214 configured to be coupled between diluent gas source 112 and conduit(s) 182 between container 114 and negative pressure source 118 to permit fluid communication of diluent gas between diluent gas source 112 and therapeutic gas effluent exiting outlet 178 of container 114. For example, therapeutic gas effluent within conduit(s) 182 can mix with diluent gas supplied by diluent gas source 112 (e.g., via third diluent conduit(s) 214) to reduce the purity of oxygen within therapeutic gas effluent. In this way and others, the concentration of oxygen within therapeutic gas effluent can be reduced to approximately 20 percent before the mixture of therapeutic gas effluent and diluent gas enters inlet 154 of negative pressure source 118.

Diluent gas source 112 can be configured to deliver diluent gas to chamber 166 (e.g., without any intermediary conduit(s) (e.g., 174) and/or port(s) (e.g., 94a and/or 94b)). As shown, diluent gas source 112 can be configured to be coupled to container 114. For example, system 10 can comprise one or more fourth diluent conduits 218 configured to be coupled between diluent gas source 112 and container 114 to permit fluid communication of diluent gas between the diluent gas source and chamber 166.

Container 114 may be configured to encourage the dilution of therapeutic gas effluent within chamber 166 at least by encouraging the mixing of diluent gas and therapeutic gas effluent within the chamber. For example, chamber 166 can comprise one or more baffles, impellers, a screw mixer, and/or the like to encourage mixing of diluent gas and therapeutic gas effluent within the chamber, thereby diluting the therapeutic gas effluent (i.e., decreasing the purity of oxygen within gas that exits outlet 178 of container 114). Container 114 may include an oxygen-sorbent material 222 disposed within chamber 166 to encourage the dilution of therapeutic gas effluent within the chamber. For example, oxygen-sorbent material 222 can comprise one or more elements selected from the group of elements consisting of: iron, sodium chloride, and activated carbon. Further, container 114 may include one or more oxygen filters 226 within chamber 166 to absorb oxygen, thereby diluting therapeutic gas effluent within the chamber. At least one of oxygen filter(s) 226 can be impregnated with one or more elements selected from the group of elements consisting of: pyrogallol, iron, silver chloride, ascorbic acid, and/or the like, to dilute therapeutic gas effluent within chamber 166.

In some embodiments, diluent gas comprises atmospheric air to dilute therapeutic gas effluent. For example, system 10 may comprise one or more openings, each of which may be filtered (e.g., 110) and exposed to atmospheric air such that, when negative pressure source 118 is activated to draw fluid (e.g., therapeutic gas effluent and/or exudate) from interior volume 78, the negative pressure source draws atmospheric air into one or more conduit(s) (e.g., 174, 182, 190, 214, 218), into diluent gas source 112, and/or into chamber 166, via the filtered openings. For example, diluent gas source 112 can comprise a one-way valve 230 in fluid communication with chamber 166 and configured to permit communication of diluent gas (e.g., atmospheric air) into the chamber through the valve and prevent communication of the diluent gas out of the chamber through the valve. For further example, container 114 can comprise a one-way valve 234 in fluid communication with chamber 166 and configured to permit communication of diluent gas (e.g., atmospheric air) into the chamber through the valve and prevent communication of the diluent gas out of the chamber through the valve.

System 10 can comprise one or more safety features configured to prevent the propagation of fire in the event conduit(s) 130, 174, 182, carrying therapeutic gas and/or therapeutic gas effluent catch fire. For example, at least one of TG conduit(s) 130 and/or effluent conduit(s) 174 can comprise one or more safety valves 238 configured to block fluid communication in the respective conduit through the valve in response to detecting a fire within the respective conduit. Each safety valve 238 may block fluid communication in a respective conduit (e.g., 130, 174) by having a material that melts in response to a temperature within the conduit exceeding a threshold level. The melted material can be configured to block fluid flow through the respective conduit. In this way and others, valve(s) 238 can reduce the risk of a fire reaching therapeutic gas source 106, can reduce the rate at which a fire spreads along TG and effluent conduit(s) 130, 174, and/or the like.

Optionally, device 14 can include a wound irrigation device 122 configured to provide wound irrigation fluid to dressing 18. Such a wound irrigation fluid can comprise any suitable substance configured to sterilize and/or disinfect target tissue 22, such as, for example, one or more elements selected from the group consisting of saline, an antimicrobial, and bleach. Wound irrigation device 122 may be configured to be in fluid communication with interior volume 78 to provide wound irrigation fluid to the interior volume. More particularly, device 14 may comprise a third outlet 242 configured to be in fluid communication with wound irrigation device 122. System 10 may comprise one or more irrigation conduits 246 configured to be coupled between wound irrigation device 122 and dressing 18, such as, for example, via third outlet 242, to permit fluid communication of wound irrigation fluid between wound irrigation device 122 and dressing 18 (e.g., interior volume 78). For example, inlet port(s) 94b of body 134 may comprise a second inlet 250 configured to be in fluid communication with interior volume 78 and to receive wound irrigation fluid from wound irrigation device 122. For example, second inlet 250 can comprise a one-way valve 254 configured to permit communication of wound irrigation fluid into interior volume 78 through the valve and prevent communication of fluid out of the interior volume through the valve.

In some embodiments, first outlet 126 and third outlet 242 of device 14 may be integral and incorporated into a single outlet (e.g., 126) having a valve movable between a first position, in which the valve permits therapeutic gas from therapeutic gas source 106 through the outlet, and a second position, in which the valve permits wound irrigation fluid from wound irrigation device 122 through the outlet.

Figure 2:
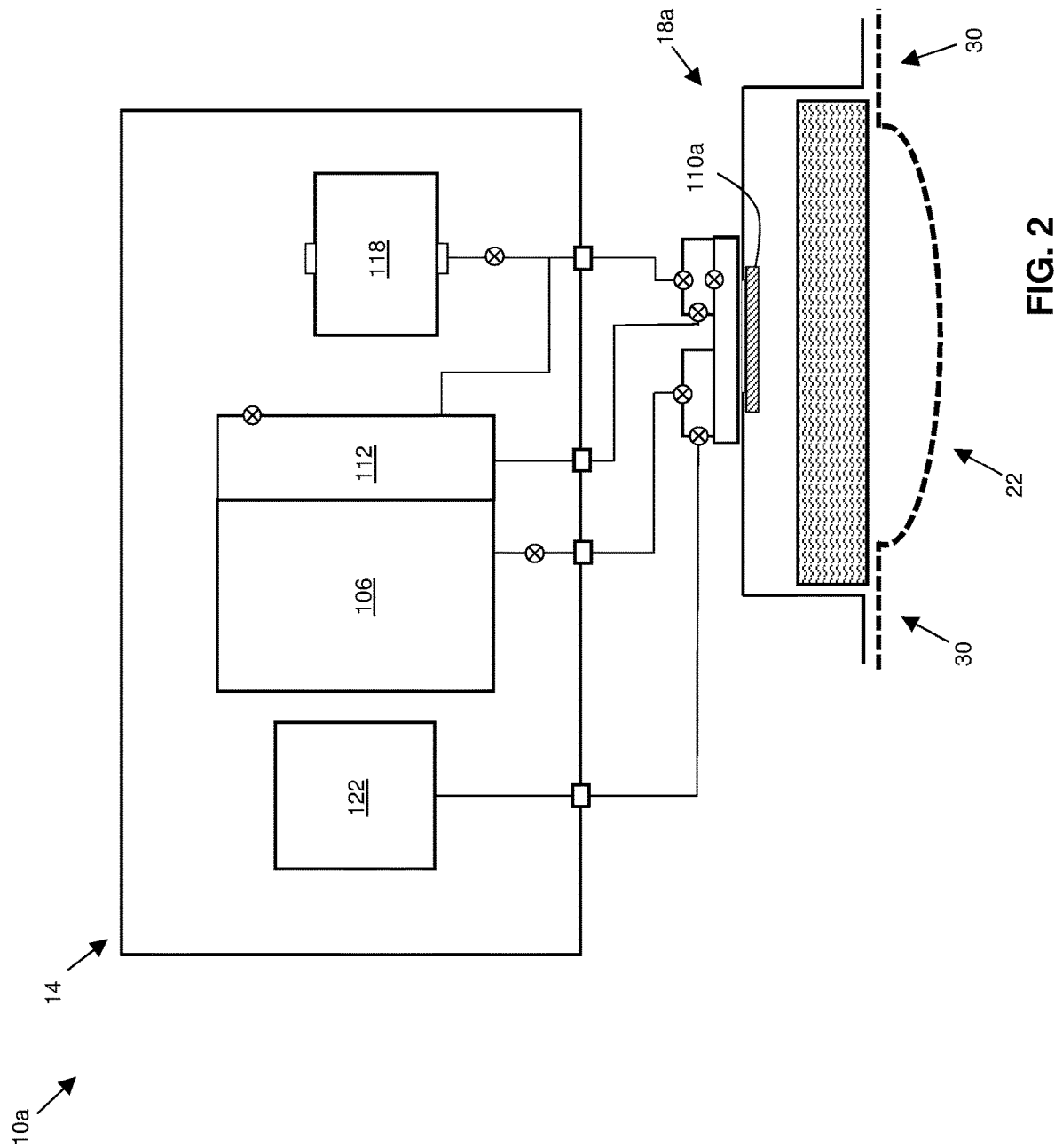
FIG. 2 is a schematic view of a second embodiment of the present systems.

Referring now to FIG. 2, shown therein and designated by the reference numeral 10a is a second embodiment of the present systems. System 10a is substantially similar to system 10, with the primary exception that system 10a does not have a container (e.g., 144) within housing 102 of device 14. As shown, system 10a comprises a dressing 18a that is substantially similar to dressing 18, with the primary exception that dressing 18a comprises a filter 110a, which is substantially similar to filter 110. Filter 110a can be coupled to an upper surface or a lower surface of gas occlusive layer 74. One or more outlet port(s) 94a of body 134 may comprise filter 110a. Filter 110a is configured to filter fluid that flows through outlet port(s) 94*a*. Filter 110*a* is configured to permit communication of therapeutic gas effluent out of interior volume 78 through port(s) 94*a* and restrict communication of exudate out of the interior volume through the port(s). As shown, negative pressure source 118 can be configured to be in fluid communication with dressing 18*a* such that the negative pressure source can be activated to draw therapeutic gas effluent from interior volume 78. In other words, filter 110*a* of dressing 18*a* can prevent exudate from flowing out of interior volume 78, and thereby prevent exudate from flowing to negative pressure source 23.

Some embodiments of the present methods for diluting therapeutic gas effluent flowing from a dressing (e.g., 18) coupling a dressing (e.g., 18) to a patient's tissue (e.g., 22 or 30), the dressing comprising a gas-occlusive layer (e.g., 74) configured to be coupled to tissue e.g., 30) surrounding target tissue (e.g., 22) such that an interior volume (e.g., 78) is defined between the gas-occlusive layer and the target tissue; providing therapeutic gas to the interior volume; removing therapeutic gas effluent from the interior volume; and mixing the removed therapeutic gas effluent with a diluent gas.

In some embodiments of the present methods, the removed therapeutic gas effluent is mixed with the diluent gas in a container (e.g., 114) outside the interior volume. In some embodiments of the present methods, the therapeutic gas effluent is removed from the interior volume by applying a negative pressure within the interior volume. In some embodiments of the present methods, providing therapeutic gas to the interior volume and removing therapeutic gas effluent from the interior volume occurs simultaneously. In some embodiments of the present methods, providing therapeutic gas and removing therapeutic gas effluent occurs simultaneously for a duration of 3 to 4 hours. Some embodiments of the present methods comprise providing wound irrigation fluid to the interior volume. In some embodiments of the present methods, the wound irrigation fluid is provided for a duration of 5 to 15 minutes. Some embodiments of the present methods comprise removing wound irrigation fluid from the interior volume.

The above specification and examples provide a complete description of the structure and use of illustrative embodiments. Although certain embodiments have been described above with a certain degree of particularity, or with reference to one or more individual embodiments, those skilled in the art could make numerous alterations to the disclosed embodiments without departing from the scope of this invention. As such, the various illustrative embodiments of the methods and systems are not intended to be limited to the particular forms disclosed. Rather, they include all modifications and alternatives falling within the scope of the claims, and embodiments other than the one shown may include some or all of the features of the depicted embodiment. For example, elements may be omitted or combined as a unitary structure, and/or connections may be substituted. Further, where appropriate, aspects of any of the examples described above may be combined with aspects of any of the other examples described to form further examples having comparable or different properties and/or functions, and addressing the same or different problems. Similarly, it will be understood that the benefits and advantages described above may relate to one embodiment or may relate to several embodiments.

The claims are not intended to include, and should not be interpreted to include, means-plus- or step-plus-function limitations, unless such a limitation is explicitly recited in a given claim using the phrase(s) "means for" or "step for," respectively.

The invention claimed is:

1. A device configured to dilute therapeutic gas effluent flowing from a dressing, the device comprising:
   a therapeutic gas source configured to provide therapeutic gas to the dressing;
   a first outlet configured to be in fluid communication with the therapeutic gas source;
   a container comprising a sidewall that defines a chamber configured to receive the therapeutic gas effluent from the dressing;
   a first inlet configured to be in fluid communication with the chamber and to receive the therapeutic gas effluent from the dressing;
   a negative pressure source configured to be coupled to the container such that the negative pressure source can be activated to draw fluid from the dressing through the chamber of the container, wherein the negative pressure source comprises:
   an inlet through which gas is received into the negative pressure source; and an outlet through which gas exits the negative pressure source;
   a diluent gas source configured to deliver a diluent gas to dilute the therapeutic gas effluent before the therapeutic gas effluent enters through the inlet of the negative pressure source;
   wherein the therapeutic gas source comprises oxygen from an oxygen source that includes an oxygen concentrator configured to receive atmospheric air and remove nitrogen from the air; and
   wherein the diluent gas comprises the nitrogen removed by the oxygen concentrator.

2. The device of claim 1, wherein the diluent gas source is integral with the therapeutic gas source.

3. The device of claim 1, wherein the chamber comprises an oxygen-sorbent material having one or more elements selected from the group of elements consisting of: iron, sodium chloride, and activated carbon.

4. The device claim 1, wherein the container comprises one or more oxygen filters configured to absorb oxygen, the one or more oxygen filters being impregnated with one or more elements selected from the group of elements consisting of: pyrogallol, iron, silver chloride, and ascorbic acid.

5. The device of claim 1, where the diluent gas source comprises a reservoir containing the diluent gas, wherein the reservoir is configured to be coupled to the container in fluid communication with the chamber to provide the diluent gas to the chamber.

6. The device of claim 1, wherein the diluent gas comprises nitrogen.

7. The device of claim 1, comprising one or more effluent conduits configured to be coupled to the first inlet to permit fluid communication of the therapeutic gas effluent between the dressing and the chamber.

8. The device of claim 7, comprising one or more first diluent conduits configured to be coupled between the diluent gas source and at least one of the one or more effluent conduits to permit fluid communication of the diluent gas between the diluent gas source and the chamber.

9. The device of claim 1, comprising one or more second diluent conduits configured to be coupled between the diluent gas source and the container to permit fluid communication of the diluent gas between the diluent gas source and the chamber.

10. The device of claim 1, comprising:
- a second outlet configured to be in fluid communication with the diluent gas source;
- one or more third diluent conduits configured to be coupled to the second outlet to permit fluid communication of the diluent gas between the diluent gas source and the dressing.

11. The device of any of claim 1, comprising one or more fourth diluent conduits configured to be coupled between the diluent gas source and the negative pressure source to permit fluid communication of the diluent gas between the diluent gas source and the negative pressure source.

12. The device of claim 1, comprising a wound irrigation device configured to provide wound irrigation fluid to the dressing.

13. A device configured to dilute therapeutic gas effluent flowing from a dressing, the device comprising:
- a therapeutic gas source configured to provide therapeutic gas to the dressing;
- a first outlet configured to be in fluid communication with the therapeutic gas source;
- a container comprising a sidewall that defines a chamber configured to receive the therapeutic gas effluent from the dressing;
- a first inlet configured to be in fluid communication with the chamber and to receive the therapeutic gas effluent from the dressing;
- a negative pressure source configured to be coupled to the container such that the negative pressure source can be activated to draw fluid from the dressing through the chamber of the container, wherein the negative pressure source comprises:
- an inlet through which gas is received into the negative pressure source; and an outlet through which gas exits the negative pressure source;
- a diluent gas source configured to deliver a diluent gas to dilute the therapeutic gas effluent before the therapeutic gas effluent enters through the inlet of the negative pressure source;
- wherein the therapeutic gas source comprises an oxygen source and the therapeutic gas comprises oxygen, and the chamber comprises an oxygen-sorbent material having one or more elements selected from the group of elements consisting of: iron, sodium chloride, and activated carbon.

14. The device of claim 13, wherein the diluent gas source is integral with the therapeutic gas source.

15. A device configured to dilute therapeutic gas effluent flowing from a dressing, the device comprising:
- a therapeutic gas source configured to provide therapeutic gas to the dressing;
- a first outlet configured to be in fluid communication with the therapeutic gas source;
- a container comprising a sidewall that defines a chamber configured to receive the therapeutic gas effluent from the dressing;
- a first inlet configured to be in fluid communication with the chamber and to receive the therapeutic gas effluent from the dressing;
- a negative pressure source configured to be coupled to the container such that the negative pressure source can be activated to draw fluid from the dressing through the chamber of the container, wherein the negative pressure source comprises:
- an inlet through which gas is received into the negative pressure source; and an outlet through which gas exits the negative pressure source;
- a diluent gas source configured to deliver a diluent gas to dilute the therapeutic gas effluent before the therapeutic gas effluent enters through the inlet of the negative pressure source;
- wherein the therapeutic gas source comprises an oxygen source and the therapeutic gas comprises oxygen and the container comprises one or more oxygen filters configured to absorb oxygen, the one or more oxygen filters being impregnated with one or more elements selected from the group of elements consisting of: pyrogallol, iron, silver chloride, and ascorbic acid.

16. The device of claim 15, where the diluent gas source comprises a reservoir containing the diluent gas, wherein the reservoir is configured to be coupled to the container in fluid communication with the chamber to provide the diluent gas to the chamber.

* * * * *